United States Patent
Kim et al.

(10) Patent No.: US 8,438,932 B2
(45) Date of Patent: May 14, 2013

(54) INSTRUMENT FOR TORSION MOMENT TEST OF SINGLE-POLE CYLINDRICAL FOUNDATION

(75) Inventors: Dae Hong Kim, Daejeon (KR); Gi Dae Oh, Daejeon (KR); Dae Soo Lee, Daejeon (KR); Kyoung Yul Kim, Daejeon (KR); Sung Yun Hong, Daejeon (KR); Moo Sung Ryu, Daejeon (KR); Dae Hak Kim, Seoul (KR)

(73) Assignee: Korea Electric Power Corporation, Gangnam-Gu, Seoul (KR)

( * ) Notice: Subject to any disclaimer, the term of this patent is extended or adjusted under 35 U.S.C. 154(b) by 209 days.

(21) Appl. No.: 12/882,543

(22) Filed: Sep. 15, 2010

(65) Prior Publication Data

US 2011/0072908 A1    Mar. 31, 2011

(51) Int. Cl.
*G01N 3/22* (2006.01)
(52) U.S. Cl.
USPC .............................................. 73/847; 73/760
(58) Field of Classification Search .................. 73/760, 73/826, 847
See application file for complete search history.

(56) References Cited

U.S. PATENT DOCUMENTS

| | | | |
|---|---|---|---|
| 4,479,800 A | * | 10/1984 | Chester .......................... 604/187 |
| 4,602,259 A | * | 7/1986 | Shepard ......................... 342/359 |
| 5,051,919 A | * | 9/1991 | Deuar .............................. 702/43 |
| 5,342,267 A | * | 8/1994 | Adams et al. ................... 482/83 |
| 8,256,184 B2 | * | 9/2012 | Lowe .......................... 52/741.3 |

FOREIGN PATENT DOCUMENTS

JP    60-120228    6/1985

OTHER PUBLICATIONS

English Abstract of JP60-120228, Dated Jun. 27, 1985.
Dae-Hong Kim, Kyoung-Yul Kim, Experimental Study on the Laterally Loaded Behavior of Single Pole Foundation, pp. 1087-1094, Thesis—Spring National Conference Mar. 28-29, 2008, Seoul, Korea.
Korean Office Action in related Patent Application No. 10-2009-0091193, Dated Jun. 21, 2011.

* cited by examiner

*Primary Examiner* — Max Noori
(74) *Attorney, Agent, or Firm* — McClure, Qualey & Rodack, LLP

(57) ABSTRACT

The present invention relates to an instrument for measuring torsion moment per a single-pole cylindrical foundation, including: a force-applying means that applies horizontal force to structures protruding from the ground; a tension means that is connected with the force-applying means to apply tensile force to the structures; a measuring unit that is disposed inside the structures to measure strain per depth and portion due to force applied from the force-applying means and the tension means; and a controller that analyzes moment per depth of the structures from horizontal force measured by the measuring unit.

5 Claims, 3 Drawing Sheets

INSTRUMENT FOR TORSION MOMENT TEST OF SINGLE-POLE CYLINDRICAL FOUNDATION

CROSS-REFERENCE TO RELATED APPLICATION

This application claims priority to and the benefit of Korean Patent Application No. 10-2009-0091193 filed in the Korean Intellectual Property Office on Sep. 25, 2009, the entire contents of which are incorporated herein by reference.

BACKGROUND OF THE INVENTION

1. Field of the Invention

The present invention relates to an instrument for torsion moment test of a single-pole cylindrical foundation, and more particularly, to an instrument for torsion moment test of a single-pole cylindrical foundation that measures overturning moment and torsion moment, and a method of measuring torsion moment for a single-pole cylindrical foundation.

2. Description of the Related Art

Vertical compression force, vertical tensile force, and horizontal force are generally exerted in the piles of bridge foundations or building foundations. A compression & vertical load test, a tension load test, and a lateral load test are used to ensure stability of the ground for the bridge foundations or building foundations. The test standard is regulated and enforced by ASTM and KS has regulated and enforced a domestic standard for a pile vertical compression test. However, not the vertical compression force, vertical-horizontal force, or vertical tensile force, but overturning moment and torsion moment (FIG. 2) are mainly exerted in a structure, such as a short single pole with the foundation protruding from the ground, a milepost, a street lamp, a traffic signal, a foundation pile-integrated pier (FIG. 2), but there is no detailed test method for this.

SUMMARY OF THE INVENTION

The present invention has been made in an effort to provide an instrument for torsion moment test of a single-pole cylindrical foundation which analyze torsion load in a foundation structure protruding from the ground and support behavior of the foundation and the ground for depth.

An exemplary embodiment of the present invention provides an instrument for measuring torsion moment for a single-pole cylindrical foundation, includes: a force-applying means that applies horizontal force to structures protruding from the ground; a tension means that is connected with the force-applying means to apply tensile force to the structures; a measuring unit that is disposed inside the structures to measure strain per depth and portion due to force applied from the force-applying means and the tension means; and a controller that analyzes moment per depth of the structures from horizontal force measured by the measuring unit.

According to the exemplary embodiment of the present invention, it is possible to check and analyze support behavior in accordance with moment exerted in the foundation of a structure protruding from the ground, and the ground. Therefore, it is possible to ensure stability in an economical design application and use with respect to moment of the structures protruding from the ground.

DETAILED DESCRIPTION OF THE EMBODIMENTS

Figure 1:
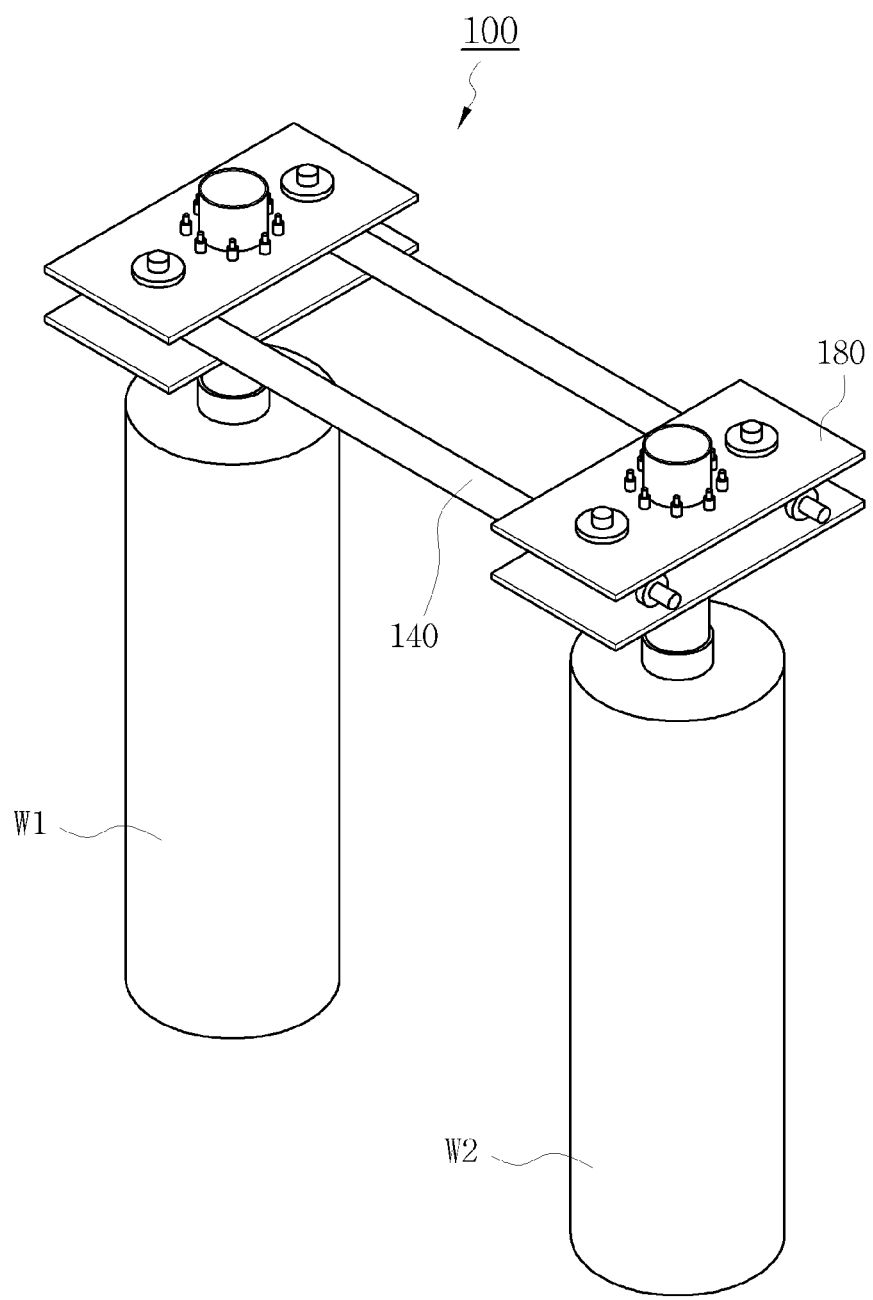
FIG. 1 is a perspective view showing an exemplary embodiment of an instrument for torsion moment test of a single-pole cylindrical foundation according to the present invention.
Figure 2:
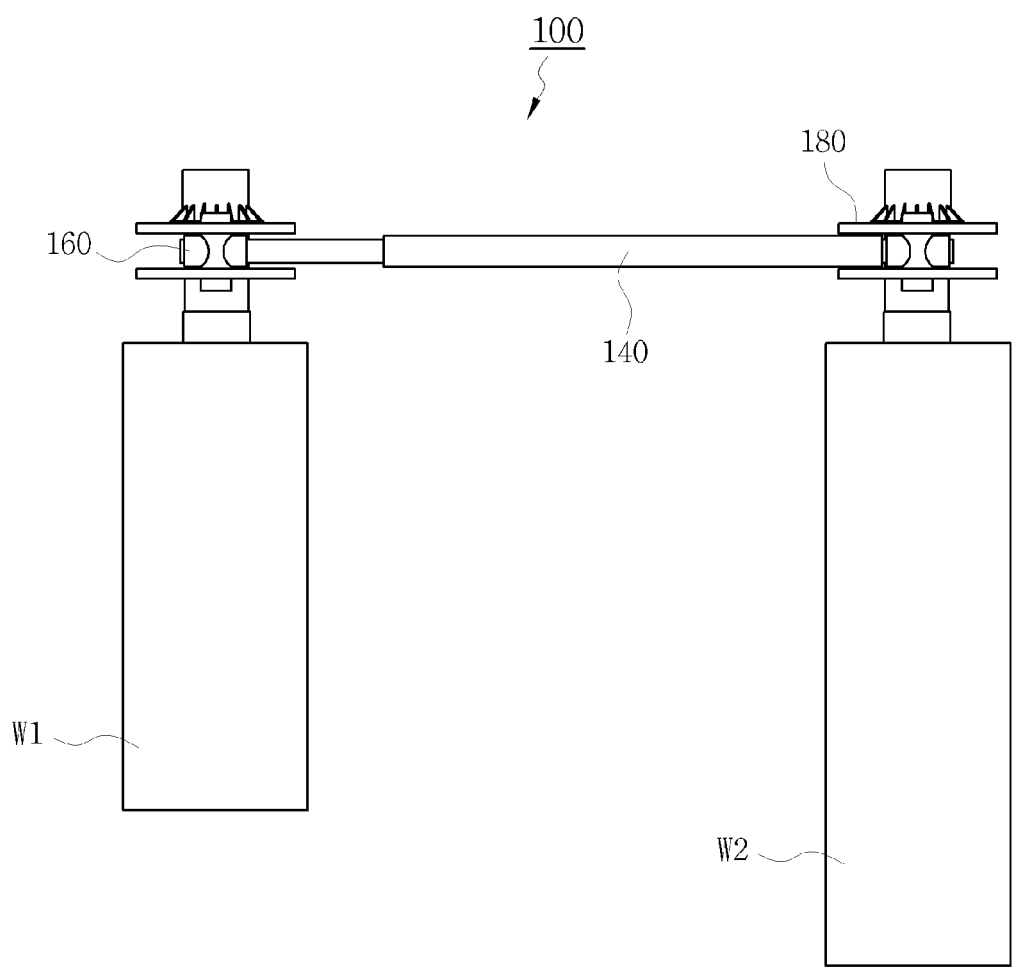
FIG. 2 is a side view showing the side of FIG. 1.

FIG. 1 is a perspective view showing an exemplary embodiment of an instrument 100 for torsion moment test of a single-pole cylindrical foundation according to the present invention. FIG. 2 is a side view showing the side of FIG. 1.

Referring to FIGS. 1 and 2, the instrument 100 for torsion moment test of a single-pole cylindrical foundation includes tension means 140 each having one end connected with structures W1 and W2 protruding from the ground. A force-applying means (not shown) supplying horizontal force by independently applying moment to the structures W1 and W2 through the tension means 140 is connected to the other end of each of the tension means 140.

The force-applying means may include a hydraulic cylinder or a wrench etc. The stroke distance of the force-applying means is set enough to carry out a test until the ground is destroyed or the structures are destroyed.

The force-applying means may be differently applied in accordance with a force-applying method. Further, when applying horizontal force, the force-applying means may include banking, cutting, and constructing a platform.

The force-applying means and the structures W1 and W2 are connected by the tension means 140. The tension means 140 may include a cylinder.

Further, a load gauge 160 disposed between the force-applying means and the structures W1 and W2 to measure applied load. The load gauge 160 can check the load and control the magnitude and increase speed of the load, when force is applied.

A strain gauge (not shown) that measures strain per depth and portion is disposed inside the structures W1 and W2. Further, a controller (not shown) that analyzes moment per depth from horizontal force measured by the strain gauge is included inside the structures W1 and W2.

Further, the instrument 100 for torsion moment test per a single-pole cylindrical foundation may further include an automatic clinometer (not shown) that measures torsion behavior per depth, in the lower portion of the structure.

The instrument 100 for torsion moment test of a single-pole cylindrical foundation may include a force-applying plate 180 disposed on the top of the structures W1 and W2.

When the structures W1 and W2 are single poles, controller 110 of the force-applying plate 180 can be fixed by the single poles. Further, the structure W1 and W2 are solids, the force-applying part may be manufactured or may be formed by a specific boring process.

Figure 3:
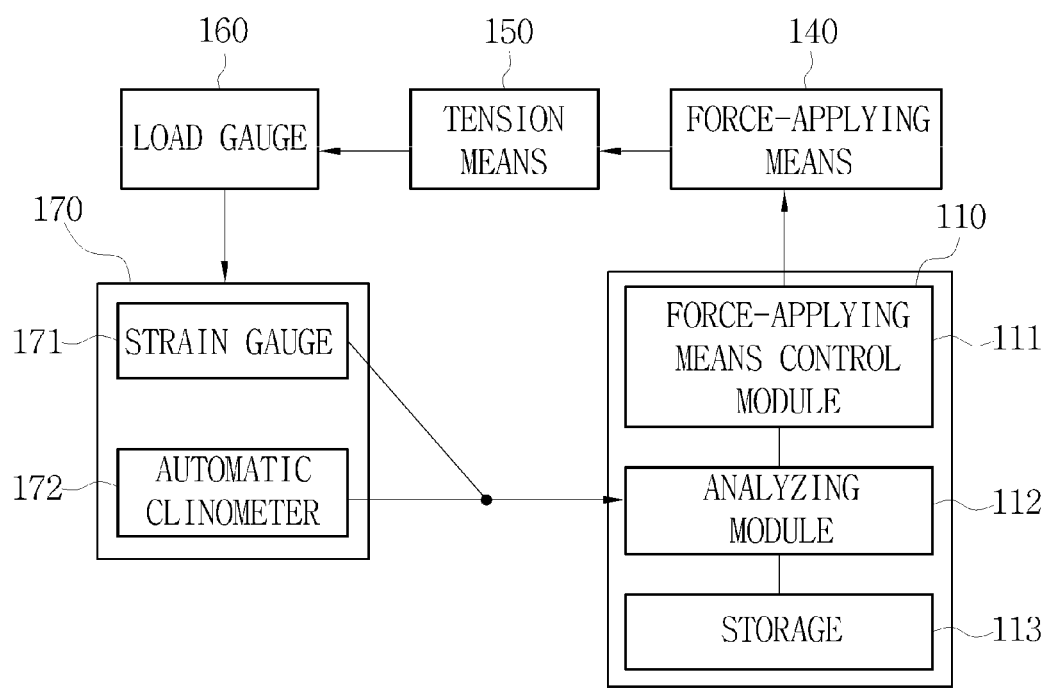
FIG. 3 is a block diagram illustrating the control flow in the instrument for torsion moment test of a single-pole cylindrical foundation shown in FIG. 1.

FIG. 3 is a block diagram illustrating the control flow in the instrument 100 for torsion moment test of a single-pole cylindrical foundation shown in FIG. 1.

Referring to FIG. 3, the controller 110 includes a force-applying control module 111 that controls horizontal force applied from the force-applying means 140. The controller 110 includes an analyzing module 112 that analyzes moment and ground behavior from the values measured from the strain gauge 171 and the automatic clinometer.

The controller 110 may include a storage 113 that stores the design moment of the structures and horizontal displacement values. The storage 113 may be independently formed. The} storage 113 may be variously selected. For example, the storage 113 may include an USB memory, a flash memory, and a hard disk etc.

A user installs the strain gauges 171 symmetrically at the force-applying portion and the opposite side in the structures. The user installs the strain gauges 171 for each depth of the structures W1 and W2.

The strain gauge 171 measures strain for depth of the tensed portion and the compressed portion, when moment is exerted, and converts it into stress per depth.

The strain gauge 171 converts the stress per depth into moment per depth. The moment per depth is set when the structures W1 and W2 are designed and compared with values set in advance in the storage 113.

Meanwhile, the automatic clinometer 172 calculates horizontal displacement per depth from an inclination per depth that is obtained through a moment test. The horizontal displacement per depth is compared with horizontal displacement stored in the storage 113 when designing the structures.

Therefore, it is possible to easily know the ground behavior of the structures W1 and W2 by integrally analyzing the measured data. Further, it is possible to ensure stability in economical design application and use with respect to moment of the structures protruding from the ground.

What is claimed is:

1. An instrument for measuring torsion moment of a single-pole cylindrical foundation, comprising:
    a force-applying means that applies horizontal force to structures protruding from the ground;
    a tension means that is connected with the force-applying means to apply tensile force to the structures;
    a measuring unit that is disposed inside the structures to measure strain per depth and portion due to force applied from the tension means;
    a controller that analyzes moment per depth of the structures from horizontal force measured by the measuring unit;
    a load gauge that measures applied load at the ioint between the top of the structures and the tension means, wherein the load gauge checks the load and controls the magnitude and the rate at which the load is applied from the force-applying means; and
    an automatic clinometer that measures horizontal behavior per depth, in the lower portion of the structures;
    wherein the controller includes:
    a force-applying means control module that controls force applied to the force-applying means;
    an analyzing module that analyzes moment and ground behavior from the values measured by the strain gauge and the automatic clinometer; and
    a storage that stores the moment and horizontal displacement when the structures are designed.

2. The instrument for measuring torsion moment for a single-pole cylindrical foundation according to claim 1, wherein stress per depth is converted from strain per depth at the tensed portion and the compressed portion which is measured by the strain gauge, when moment is exerted in the force-applying means, and converted moment per depth is compared with a value set when the structures are designed.

3. The instrument for measuring torsion moment per a single-pole cylindrical foundation according to claim 1, wherein the tension means includes at least one of a steel bar and a cylinder.

4. The instrument for measuring torsion moment per a single-pole cylindrical foundation according to claim 1, wherein the force-applying means includes at least one of a hydraulic cylinder and a wrench.

5. The instrument for measuring torsion moment per a single-pole cylindrical foundation according to claim 1, further comprising a force-applying plate that passes through the upper portion of the structures.

\* \* \* \* \*